United States Patent [19]

Takemura et al.

[11] 4,002,069
[45] Jan. 11, 1977

[54] MEASURING LANCE FOR MOLTEN METAL SUCH AS STEEL

[75] Inventors: Yozo Takemura, Tohkai; Eisuke Akiyoshi; Hiroshi Matsukubo, both of Aichi; Toshihiko Shibata, Tohkai, all of Japan

[73] Assignee: Nippon Steel Corporation, Tokyo, Japan

[22] Filed: May 14, 1975

[21] Appl. No.: 577,160

[52] U.S. Cl. .............................. 73/354; 73/DIG. 9
[51] Int. Cl.² .......................................... G01K 13/12
[58] Field of Search ........................ 73/DIG. 9, 354

[56] References Cited

UNITED STATES PATENTS

| | | | |
|---|---|---|---|
| 2,999,121 | 9/1961 | Mead | 136/234 |
| 3,055,961 | 9/1962 | Robertson | 136/234 |
| 3,460,393 | 8/1969 | Putnam | 73/DIG. 9 |
| 3,463,005 | 8/1969 | Hance | 73/DIG. 9 |
| 3,559,452 | 2/1971 | Perbix | 73/DIG. 9 |
| 3,685,359 | 8/1972 | Boron et al. | 73/DIG. 9 |
| 3,709,040 | 1/1973 | Coe | 73/354 |

*Primary Examiner*—S. Clement Swisher
*Attorney, Agent, or Firm*—Watson, Leavenworth, Kelton & Taggart

[57] ABSTRACT

An improved measuring lance to be inserted into a bath of molten metal, for example, molten steel, is disclosed having thermocouples on its tip end and in its receptacle chamber, respectively. The lance is provided with means to discharge air from inside a cover for a thermocouple in a receptacle chamber. A deoxidation chamber made of steel may be provided in the lance. Means to spray gas from around the connector of the lance may also be provided. These means assure accurate measuring of the temperature, composition, etc. of the bath.

9 Claims, 13 Drawing Figures

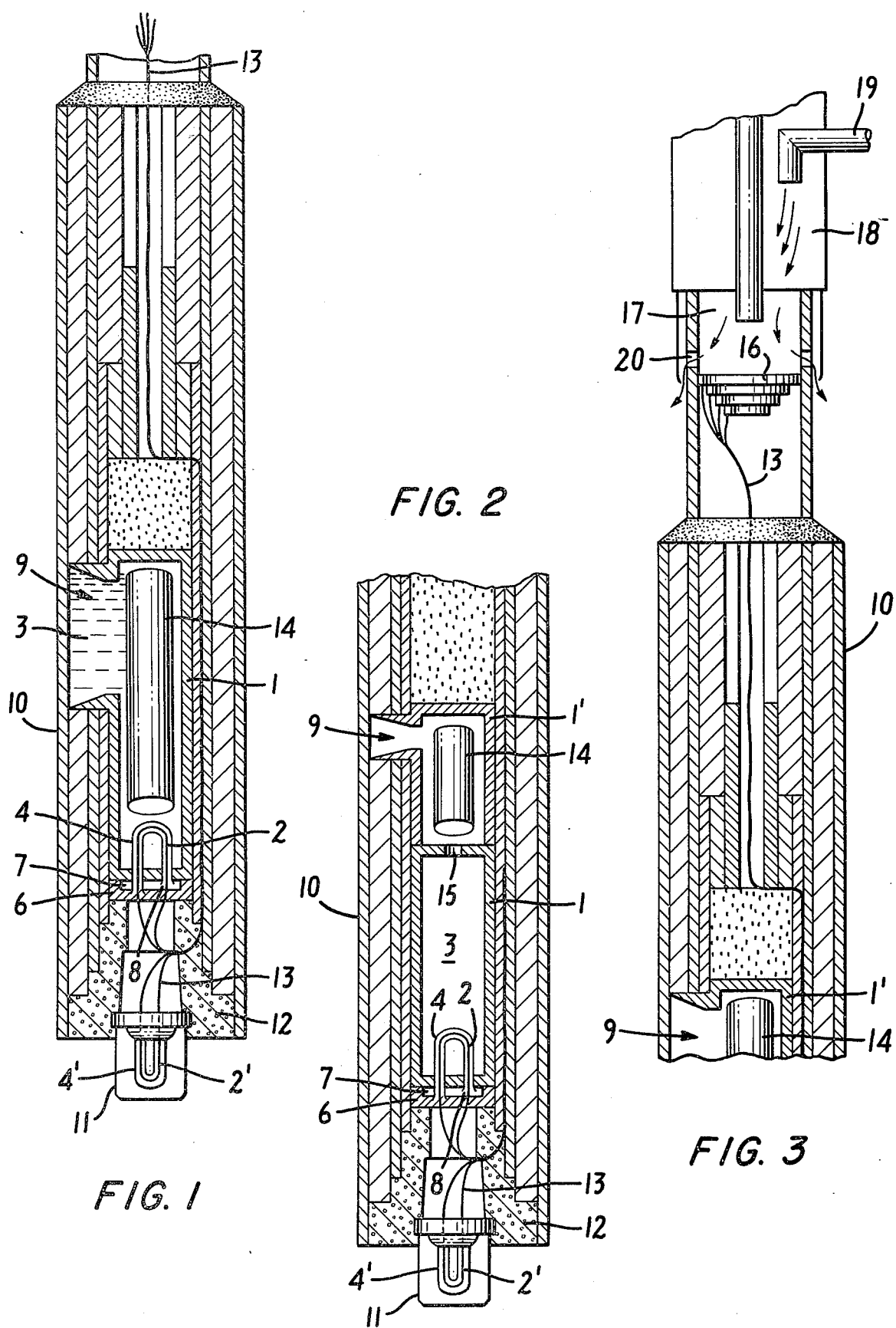

MEASURING LANCE FOR MOLTEN METAL SUCH AS STEEL

BACKGROUND OF THE INVENTION

1. Field of the Invention

This invention relates to an improved measuring lance to be inserted into a bath of molten metal, for example, molten steel, for measuring the temperature, composition, etc. of the bath.

2. Description of the Prior Art

It has been a common practice to insert a measuring lance of this kind into a molten metal, for example, a molten steel which is being refined in a converter, for retrieving a sample and measuring the composition of the steel.

The measuring lance for such purpose is generally provided with a thermocouple in its receptacle chamber for measuring the carbon content based upon the solidification temperature of the steel. An example of such measuring lance is disclosed in U.S. Pat. No. 3,685,359.

However, it often happens with such a lance that accurate measuring of the temperature of the molten steel cannot be effected for the reasons described below.

For instance, the thermocouples are protected by a tube made of hard glass of 0.5 to 1.0 mm. When it comes into contact with the molten steel, the air inside the glass tube is expanded, whereby the tube is broken, especially in its curved portion, and the air inside the tube escapes into the molten steel just sampled, which results in formation of a pipe.

When a pipe is formed like this, accurate measuring of the solidification temperature of the molten steel by the use of a thermocouple becomes difficult, which results in that accurate measuring of the carbon content in the steel cannot be carried out and in addition Count VAC analysis (analysis by vacuum optical emission spectrometer developed by Applied Research Laboratories Company) canot be effected accurately for the subsequent measuring of the other components in the steel.

The conventional measuring lance consists often of a deoxidation chamber and a receptacle chamber which are made of shell mold or casting iron. Sometimes the lance has only one chamber which serves as both the deoxidation chamber and the receptacle chamber. The invention involves both arrangements.

In the case where shell mold is used, it absorbes water because it is hygroscopic. When it comes into contact with the molten steel, the water is decomposed to thereby generate bubbles of hydrogen gas which makes it difficult to sample the molten steel. In the case where casting iron is used, a part thereof, particularly a corner part such as a mouth for taking up the molten steel, etc., is melted and entrained in the molten steel, which prevents accurate measuring of the composition of the steel.

Furthermore, the measuring lance has its outer circumference composed generally of refractory or fire-resisting papers and the like. Thus, when the lance is dipped into the molten steel, the refractory papers are naturally heated to emit vapor, tar, etc., whereby the connector to connect lance parts and the lead wires to conduct the generated electromotive force tend to be injured by the vapor or tar, etc. thereby resulting in leakage of the electromotive force and a hindering in the accurate measuring of the molten steel. In addition the tar, dust and the like tends to adhere to the connector thus resulting in an increase of contact resistance and a reading of a value lower than the actual value of the electromotive force. This, of course, prevents the accurate measuring of the molten steel.

SUMMARY OF THE INVENTION

It is therefore an object of the invention to provide an improved measuring lance capable of preventing generation of bubbles in a molten metal, for example, molten steel, sampled therein, and assuring accurate measuring of the composition, etc., of the molten metal.

It is another object of the invention to provide an improved measuring lance capable of assuring accurate measuring of the composition, etc., of the molten steel when the parts of the lance come into contact with the molten steel and the parts are melted and entrained in the molten steel.

It is still another object of the invention to provide an improved measuring lance capable of assuring accurate measuring of a molten metal, for example, molten steel, without substantial fluctuations by means of spray of a gas.

According to this invention, (embodiment A) there is provided a measuring lance to be inserted into the molten metal which comprises an expendable body, a protected first thermocouple mounted on one end of said lance, a receptacle chamber for receiving the molten metal, a protected second thermocouple mounted inside said chamber, and a path for the molten metal leading to said chamber, characterized in that an opening through which air can be discharged is provided in a part of a protecting tube for the second thermocouple, said part not positioned in said receptacle chamber.

Also according to this invention, (embodiment B) there is provided a measuring lance to be inserted into the molten metal which comprises an expendable body, a protected first thermocouple mounted on one end of said lance, a receptacle chamber for receiving the molten metal, a protected second thermocouple mounted inside said chamber, and a path for the molten metal leading to said chamber, characterized in that the air has preliminarily been discharged from inside a protecting tube for the second thermocouple.

According to this invention, there is provided a measuring lance according to embodiment A and B in which said lance is to be inserted into the molten steel and a deoxidation chamber made of steel is provided.

According to this invention, there is provided a measuring lance according to embodiment A and B in which a connector is provided and a gas spray nozzle is provided in the upper part thereof.

According to this invention, there is provided a measuring lance according to the above embodiment A in which said opening is interconnected with a vacant space.

According to this invention, there is provided a measuring lance according to the above embodiment A in which one or both ends of said protective tube are allowed to be projected outwardly from said receptacle chamber.

According to this invention, there is provided a measuring lance according to the above embodiment A in which one or both ends of said protecting tube are positioned in a porous brick which is interconnected outside said receptacle chamber.

According to this invention, there is provided a measuring lance according to embodiment B in which the protecting tube is broken or deformed to discharge the air after the second thermocouple is inserted into said tube, and thereafter said tube is mounted in said receptacle chamber.

BRIEF DESCRIPTION OF THE DRAWINGS

This invention is further described with reference to the following drawings:

FIGS. 1, 2 and 3 are sectional views illustrating the respective embodiments of the measuring lance of this invention.

FIG. 8' is an enlarged sectional view of the tube shown in FIG. 8.

DESCRIPTION OF THE PREFERRED EMBODIMENTS

Figure 4:
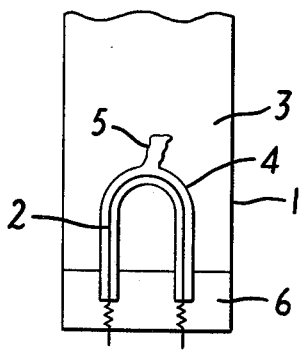
FIG. 4 is a schematic view showing a situation where bubbles occur in the molten steel.

In FIG. 1, the reference numeral 1 is a receptacle chamber, 2, 2' are thermocouples, 3 is molten steel, 4, 4' are protecting tubes, 6 is a base member, 7 is a vacant space, 8 is an opening for the discharge of air, 9 is a path for receiving the molten steel, 10 is a paper-made lance body, 11 represents a cap and 12 is a refractory cement, 13 is lead wires, 14 is an aluminum tube for deoxidation.

Figure 10:
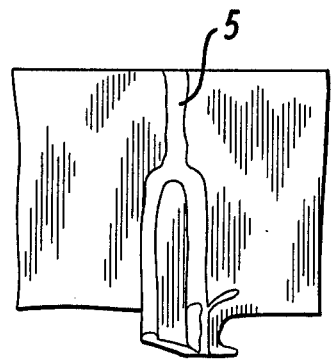
FIG. 10 is a sectional view of a steel sampled by a measuring lance of the prior art.

In the conventional sampling as shown in FIG. 4, a protecting tube 4 made of glass is broken due to expansion of air inside therein caused by contact between the molten steel 3 received inside receptacle chamber 1 and glass tube 4 protecting therocouple 2. As a result, the air enters the molten steel 3 forming a pipe 5 therein. This is also shown in FIG. 10.

In this invention, as shown in FIG. 1, an opening 8 for the discharge of air, is mounted in a part (lying outside receptacle chamber 1) of protecting tube 4 made usually of glass. In this case, the receptacle chamber is concurrently used as the deoxidation chamber, i.e., the receptacle chamber and the deoxidation chamber are the same. When the molten steel sampled in said chamber comes into contact with tube 4, the air thus expanded therein is discharged through opening 8 to the vacant space 7 outside chamber 1.

Figure 5:
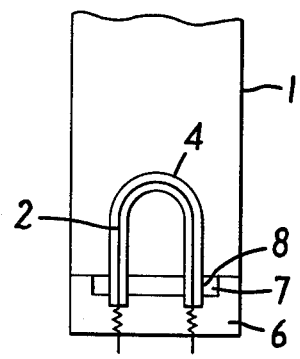
FIGS. 5, 6, and 7 are schematic views illustrating embodiments other than that of FIG. 1 of the measuring lance of this invention.
Figure 6:
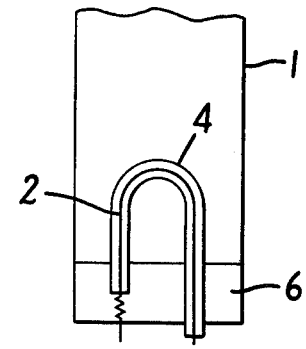
Figure 7:
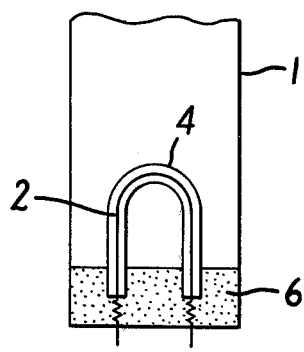

The other examples of the opening positioned are shown in FIGS. 5, 6 and 7.

In FIG. 5, opening 8 is provided in a section of the tube 4 which is interconnected with vacant space 7. Space 7 is positioned on base member 6 which lies outside receptacle chamber 1. The air expanded inside tube 4 is thus discharged from the chamber 1 through vacant space 7.

In FIG. 6, one end of tube 4 is projected downwardly from base 6 so that the expanded air can be discharged from chamber 1.

In FIG. 7, member base 6 is made of porous brick. The expanded air is led first into this porous brick or base member, and then discharged outside therefrom.

Figure 8:
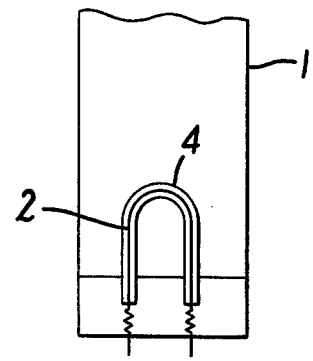
FIG. 8 is a schematic view illustrating a situation where air has been preliminarily been discharged from the protecting tube.
Figure 8:
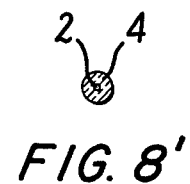

In another aspect of this invention, protecting tube 4 is preliminarily destroyed or deformed so as to expel the air therefrom, and then it is mounted in receptacle chamber 1, as shown in FIG. 8 and FIG. 8'.

Figure 9:
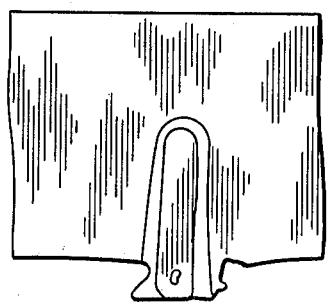
FIG. 9 is a sectional view of a steel sampled by a measuring lance of this invention.

As set forth herein above, when using a lance of this invention, there are no bubbles generated in the molten steel sampled as shown in FIG. 9, while in the case of a lance conventionally used, bubbles are generated in the molten steel sampled, forming a pipe therein as shown in FIG. 10. In the latter case, accurate measuring becomes impossible.

In the practice of this invention for sampling molten steel, a deoxidation chamber may be made of steel so as to avoid any substantial effect upon the composition of the molten steel even if a part of the chamber is melted and entrained in the molten steel. In the case where the deoxidation chamber and the receptacle chamber are one and the same, the chamber may be made of steel. In the case where the deoxidation chamber is provided separately from the receptacle chamber, the receptacle chamber may be made of cast iron since the molten steel entering the receptacle chamber is substantially cooled through the deoxidation chamber, whereby the receptacle chamber is not easily melted. Nevertheless, the receptacle chamber can be made of steel in this case as can the deoxidation chamber.

An example is shown in FIG. 2 wherein a lance body 10 is provied with a deoxidation chamber 1' and a receptacle chamber 1. The deoxidation chamber 1' is made of steel and the receptacle chamber is made of steel or cast iron. The lance body 10 is dipped into a molten steel contained in a converter which is being refined by means of a sub-lance not shown. The temperature of the molten steel can be measured by a thermocouple 2' provided at the tip end of lance body 10. The molten steel enters deoxidation chamber 1' through a path or mouth 9 thereof, where the steel comes into contact with a deoxidation agent 14 such as Al, Ti, etc. which has previously been placed in chamber 1'. The molten steel thus deoxidized enters receptacle chamber 1 through an outlet 15 where the solidification temperature of the molten steel is measured by another thermocouple 2 to determine the amount of carbon in the steel.

The lance which has thus received the molten steel is withdrawn from the bath, and the steel in the receptacle chamber 1 can be measured with respect to its composition such as Mn, S, P, etc. by the use of a Count VAC analyser.

As deoxidation chamber 1' is made of steel as above, there is hardly any adverse effect which would otherwise have been encountered by the through melting loss of a part of the deoxidation chamber 1' such as a corner of the mouth 9, the outlet 15 and the like.

As for receptacle chamber 1, there is hardly any occurance when a part thereof melts into the molten steel, since the temperature of the molten steel is somewhat lowered as it is passed from the deoxidation chamber, and also there is no corner part or notch contacting the molten steel in this case.

In the practice of this invention, a spray nozzle can be provided in the upper part of the connector.

In FIG. 3, a lance is shown wherein a receptacle chamber 1 for receiving a sampled molten steel surrounded by a lance body 10 made of refractory paper is connected to a connector 16, which is in turn connected to a sub-lance 18 via a holder 17. A spray nozzle 19 is provided at the sub-lance 18 in the upper part of the connector 16. When the lance is in operation, a gas such as oxygen, nitrogen and the like is sprayed to cool lead wires 13 and the connector 16, while water vapor or tar, etc. in the holder 17 and the sub-lance 18 can be purged from a hole 20.

In FIG. 3, numeral 1' is a deoxidation chamber, 14 is a deoxidation agent, and 9 is a path or mouth for receiving the molten steel.

Figure 11:
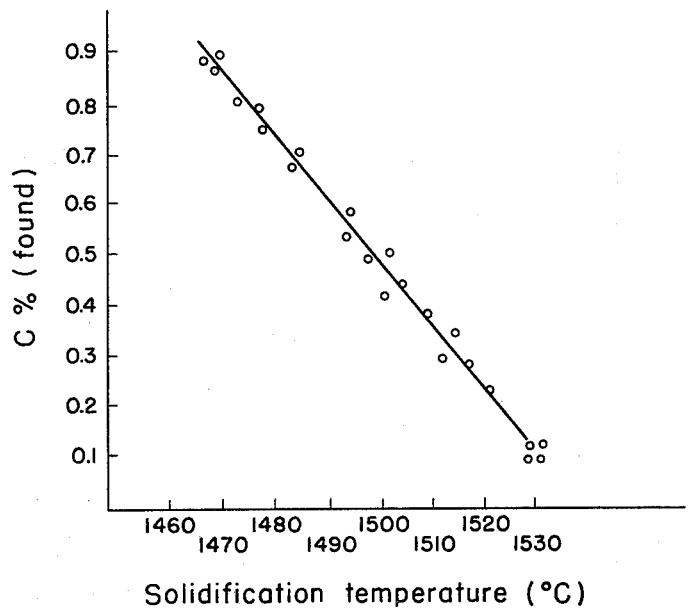
FIG. 11 is a graph showing a relation between C% and the solidification temperature measured by the use of the measuring lance shown in FIG. 3.
Figure 12:
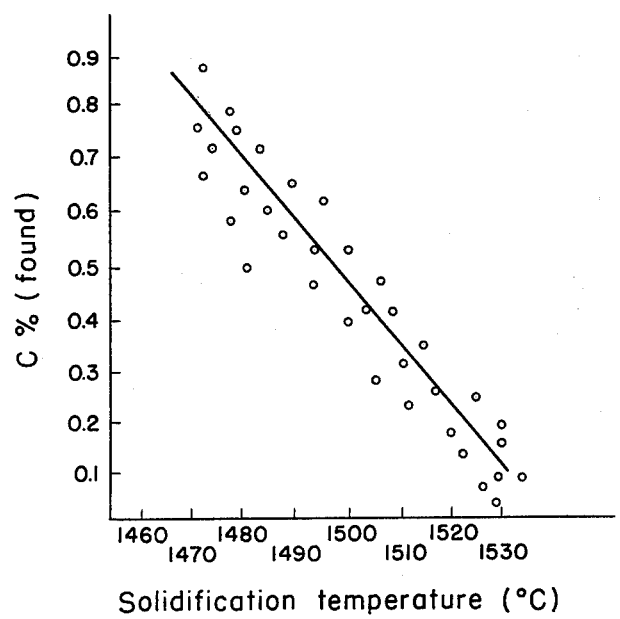
FIG. 12 is a graph showing a relation between C% and the solidification temperature measured by the use of a measuring lance of the prior art.

As explained above, water vapor, tar and the like are purged from the lance and the lead wires and the connector etc. are cooled by means of a gas spray, so that any possible disadvantage such as leakage of the electromotive force, etc. can be avoided and accurate measuring of the temperature of the molten steel can be carried out. Thus, according to a lance of this invention, accurate measuring without substantial fluctuation can be accomplished, as shown in FIG. 11, where the amount of C in the steel is derived from the solidification temperature of the molten steel. Contrary to this, when not spraying a gas, it is obvious from FIG. 12 that the resulting fluctuation is so large as to prevent accurate measuring.

We claim:

1. A measuring lance to be inserted into molten metal which comprises an expendable body, a first thermocouple protected by a first tube mounted on one end of the body, a receptacle chamber for receiving the molten metal provided inside the body, a second thermocouple protected by a second tube mounted at the bottom of said chamber and projected in the upside-down direction relative to the projecting direction of the first thermocouple, and a path for the molten metal leading to said chamber, characterized in that one or both opening ends of said second tube are positioned in a porous brick provided below the receptacle chamber.

2. A measuring lance according to claim 1 in which said molten metal is molten steel and said receptacle chamber is made of steel.

3. A measuring lance according to claim 1 in which a connector is provided in the upper part of the lance and a gas spray nozzle is provided above said connector.

4. A measuring lance to be inserted into molten metal which comprises an expendable body, a first thermocouple protected by a first tube mounted on one end of the body and projected outwardly, a receptacle chamber for receiving the molten metal provided inside the body, a second thermocouple protected by a second tube mounted at the bottom of said chamber and projected in the upside-down direction relative to the projecting direction of the first thermocouple, and a path for the molten metal leading to said chamber, characterized in that said second tube has an opening through which the air inside the second tube can be discharged, said opening being positioned below the receptacle chamber and being interconnected with a vacant space provided below said receptacle chamber, a connector being provided in the upper part of the lance and a gas spray nozzle being provided above said connector.

5. A measuring lance according to claim 4 in which said molten metal is molten steel and said receptacle chamber is made of steel.

6. A measuring lance to be inserted into molten metal which comprises an expendable body, a fist thermocouple protected by a first tube mounted on one end of the body and projected outwardly, a receptacle chamber for receiving the molten metal provided inside the body, a second thermocouple protected by a second tube mounted at the bottom of said chamber and projected in the upside-down direction relative to the projecting direction of the first thermocouple, and a path for the moten metal leading to said chamber, characterized in that said second thermocouple is closely surrounded by said second tube substantially without any air intervening between said second tube and said second thermocouple, a connector being provided in the upper part of the lance and a gas spray nozzle being provided above said connector.

7. A measuring lance according to claim 6 in which said molten metal is molten steel and said receptacle chamber is made of steel.

8. A measuring lance to be inserted into molten metal which comprises an expendable body, a first thermocouple protected by a first tube mounted on one end of the body and projected outwardly, a receptacle chamber for receiving the molten metal provided inside said body, a second thermocouple protected by a second tube mounted at the bottom of said receptacle chamber and projected in the upsidedown direction relative to the projecting direction of the first thermocouple, and a path for the molten metal leading to said chamber, characterized in that one or both opening ends of said second tube are allowed to be projected to a vacant space provided below said receptacle chamber, a connector being provided in the upper part of the lance and a gas spray nozzle being provided above said connector.

9. A measuring lance according to claim 8 in which said molten metal is molten steel and said receptacle chamber is made of steel.

* * * * *